United States Patent
Yaacobi-Gross

(10) Patent No.: US 12,122,790 B2
(45) Date of Patent: Oct. 22, 2024

(54) PHOTOACTIVE COMPOUND

(71) Applicant: Sumitomo Chemical Co., Ltd., Tokyo (JP)

(72) Inventor: Nir Yaacobi-Gross, Godmanchester (GB)

(73) Assignee: Sumitomo Chemical Co., Ltd., Tokyo (JP)

(*) Notice: Subject to any disclaimer, the term of this patent is extended or adjusted under 35 U.S.C. 154(b) by 555 days.

(21) Appl. No.: 17/297,993

(22) PCT Filed: Nov. 29, 2019

(86) PCT No.: PCT/GB2019/053392
§ 371 (c)(1),
(2) Date: May 27, 2021

(87) PCT Pub. No.: WO2020/109823
PCT Pub. Date: Jun. 4, 2020

(65) Prior Publication Data
US 2021/0395272 A1  Dec. 23, 2021

(30) Foreign Application Priority Data
Nov. 30, 2018 (GB) .................. 1819621

(51) Int. Cl.
*C07D 519/00* (2006.01)
*H10K 30/30* (2023.01)
(Continued)

(52) U.S. Cl.
CPC .......... *C07D 519/00* (2013.01); *H10K 30/30* (2023.02); *H10K 85/655* (2023.02);
(Continued)

(58) Field of Classification Search
None
See application file for complete search history.

(56) References Cited

U.S. PATENT DOCUMENTS

2019/0157581 A1   5/2019   Seifrid et al.

FOREIGN PATENT DOCUMENTS

| CN | 104557968 A | 4/2015 |
| CN | 104557968 B | 4/2017 |

(Continued)

OTHER PUBLICATIONS

Y. Lin et al., "High-performance fullerene-free polymer solar cells with 6.31% efficiency", Energy and Environmental Science 8, p. 610-616 (Year: 2015).*

(Continued)

*Primary Examiner* — Ryan S Cannon
(74) *Attorney, Agent, or Firm* — Wolf, Greenfield & Sacks, P.C.

(57) ABSTRACT

A compound of formula (I): Each $R^1$ and $R^2$ is, independently in each occurrence, a substituent. Each $R^3$-$R^{10}$ is, independently in each occurrence, H or a substituent. At least one occurrence of at least one of $R^{11}$-$R^{14}$ is CN. Each Y is independently O or S. $Z^1$-$Z^4$ are each independently a direct bond or $Z^1$, $Z^2$, $Z^3$ and/or $Z^4$ together with, respectively, $R^4$ or $R^5$, $R^7$ or $R^8$, $R^6$, or $R^9$ forms an aromatic or heteroaromatic group. The compound of formula (I) may be provided in an active layer of an organic electronic device, e.g. as an electron acceptor in a bulk heterojunction layer of an organic photodetector. A photosensor may comprise the organic photodetector and a light source, e.g. a near infra-red light source.

(Continued)

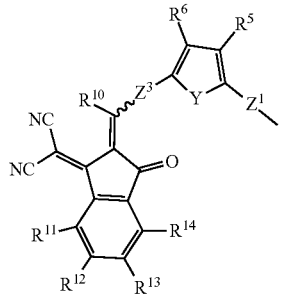

(I)

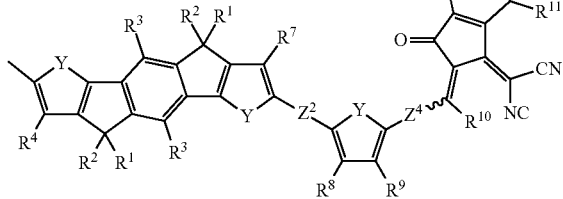

21 Claims, 5 Drawing Sheets

(51) Int. Cl.
*H10K 85/60* (2023.01)
*G01N 21/25* (2006.01)
*G01N 21/31* (2006.01)
*H10K 50/11* (2023.01)
*H10K 101/40* (2023.01)

(52) U.S. Cl.
CPC ....... *H10K 85/6576* (2023.02); *G01N 21/255* (2013.01); *G01N 21/31* (2013.01); *H10K 50/11* (2023.02); *H10K 2101/40* (2023.02)

(56) References Cited

FOREIGN PATENT DOCUMENTS

| | | |
|---|---|---|
| CN | 107814811 A | 3/2018 |
| EP | 3306690 A1 | 4/2018 |
| WO | WO-2009013491 A1 * | 1/2009 ........... G01N 21/645 |
| WO | WO 2017/191466 A1 | 11/2017 |
| WO | WO 2018/036914 A1 | 3/2018 |
| WO | WO 2018/065365 A1 | 4/2018 |
| WO | WO 2018/166232 A1 | 9/2018 |

OTHER PUBLICATIONS

M. Ans et al., "Opto-electronic properties of non-fullerene fused-undecacyclic electron acceptors for organic solar cells", Computational Materials Science 159, p. 150-159 (Year: 2019).*

International Search Report and Written Opinion dated Feb. 20, 2020 in connection with International Application No. PCT/GB2019/053392.

Combined Search and Examination Report dated May 28, 2019 in connection with GB Application No. 1819621.2.

Yao et al., Elucidating the key role of fluorine in improving the charge mobility of electron acceptors for non-fullerene organic solar cells by multiscale simulations. Journal of Materials Chemistry C. 2018;6(18):4912-8.

March et al., Reactions, Mechanisms, and Structure. Advanced Organic Chemistry. Fourth Edition. Jan. 2001. 2 Pages.

* cited by examiner

PHOTOACTIVE COMPOUND

RELATED APPLICATIONS

This Application is a national stage filing under 35 U.S.C. § 371 of international PCT application no. PCT/GB2019/053392, filed Nov. 29, 2019, which claims priority to United Kingdom patent application no. GB 1819621.2, filed Nov. 30, 2018, each of which is incorporated herein by reference in its entirety.

BACKGROUND

Embodiments of the present disclosure relate to photoactive compounds and their use in organic electronic devices, in particular organic photodetectors.

A range of organic electronic devices comprising organic semiconductor materials are known, including organic light-emitting devices, organic field effect transistors, organic photovoltaic devices and organic photodetectors (OPDs).

WO 2018/065352 discloses an OPD having a photoactive layer that contains a small molecule acceptor which does not contain a fullerene moiety and a conjugated copolymer electron donor having donor and acceptor units.

WO 2018/065356 discloses an OPD having a photoactive layer that contains a small molecule acceptor which does not contain a fullerene moiety and a conjugated copolymer electron donor having randomly distributed donor and acceptor units.

Yao et al, "Design, Synthesis, and Photovoltaic Characterization of a Small Molecular Acceptor with an Ultra-Narrow Band Gap", Angew Chem Int Ed Engl. 2017 Mar. 6; 56(11):3045-3049 discloses a non-fullerene acceptor with a band gap of 1.24 eV.

SUMMARY

A summary of aspects of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects and/or a combination of aspects that may not be set forth.

Embodiments of the present disclosure provide a compound of formula (I):

wherein:
each $R^1$ and $R^2$ is, independently in each occurrence, a substituent;
each $R^3$ is, independently in each occurrence, H or a substituent;
$R^4$-$R^9$ are, independently, H or a substituent;
each $R^{10}$ is, independently in each occurrence, H or a substituent;
each $R^{11}$-$R^{14}$ is, independently in each occurrence, H or a substituent with the proviso that at least one occurrence of at least one of $R^{11}$-$R^{14}$ is CN;
each Y is independently O or S;
$Z^1$ is a direct bond or $Z^1$, together with $R^4$ or $R^5$, forms an aromatic or heteroaromatic group $Ar^1$;
Z is a direct bond or, together with $R^7$ or $R^8$, forms an aromatic or heteroaromatic group $Ar^2$;
$Z^3$ is a direct bond or, together with $R^6$, forms an aromatic or heteroaromatic group $Ar^3$; and
$Z^4$ is a direct bond or, together with $R^9$, forms an aromatic or heteroaromatic group $Ar^4$.

The present inventors have found that compounds of formula (I) may be capable of absorbing light at long wavelengths, e.g. greater than 750 nm, optionally greater than 950 nm, optionally up to about 1500 nm allowing for use of these compounds in organic photodetectors, particularly in a photosensor containing such an OPD and a near infra-red light source.

Accordingly, in some embodiments, there is provided a composition containing an electron-accepting (n-type) compound as described herein and an electron donor (p-type) compound.

In some embodiments there formulation comprising a composition as described herein dissolved or dispersed in one or more solvents.

In some embodiments there is provided an organic photodetector having an anode; a cathode; and a photosensitive organic layer disposed between the anode and cathode.

The photosensitive organic layer may contain a donor compound and an acceptor compound of formula (I).

In some embodiments, there is provided a circuit comprising an organic photodetector as described herein, and at least one of a voltage source for applying a reverse bias to the organic photodetector and a device configured to measure photocurrent generated by the photodetector.

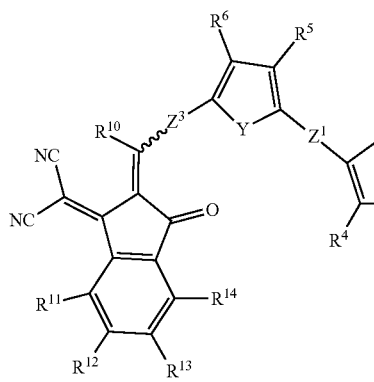
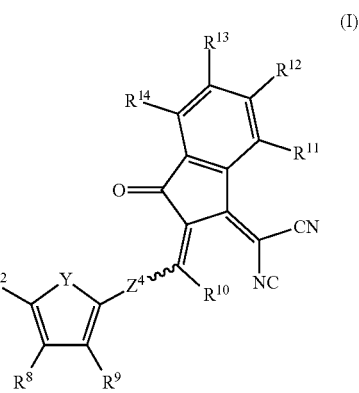

(I)

In some embodiments, there is provided a method of forming an organic photodetector as described herein comprising formation of the photosensitive organic layer over one of the anode and cathode and formation of the other of the anode and cathode over the photosensitive organic layer.

In some embodiments, there is provided a photosensor comprising a light source and an organic photodetector as described herein configured to detect light emitted from the light source.

In some embodiments, there is provided a method of determining the presence and/or concentration of a target material in a sample, the method comprising illuminating the sample and measuring a response of an organic photodetector as described herein which is configured to receive light emitted from the sample upon illumination.

DESCRIPTION OF DRAWINGS

The disclosed technology and accompanying figures describe some implementations of the disclosed technology.

Figure 1:
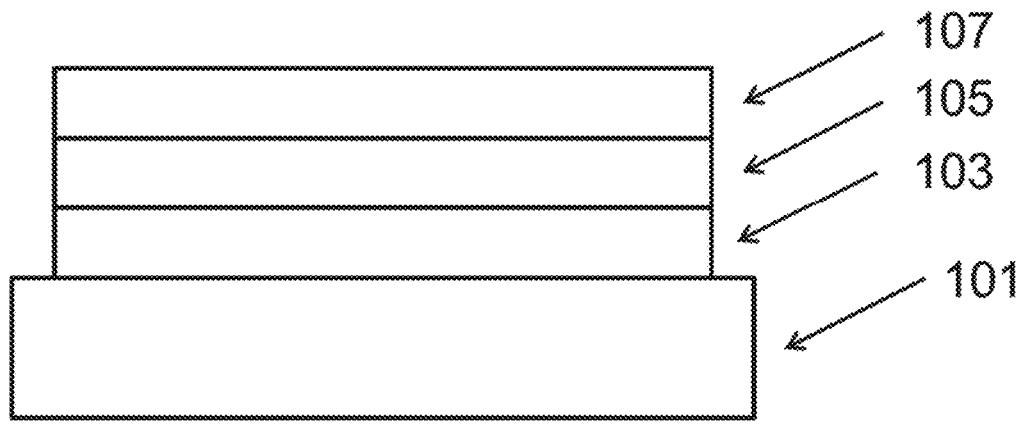
FIG. 1 illustrates an organic photodetector according to some embodiments of the present disclosure.

The drawings are not drawn to scale and have various viewpoints and perspectives. The drawings are some implementations and examples. Additionally, some components and/or operations may be separated into different blocks or combined into a single block for the purposes of discussion of some of the embodiments of the disclosed technology.

Moreover, while the technology is amenable to various modifications and alternative forms, specific embodiments have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DETAILED DESCRIPTION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, electromagnetic, or a combination thereof. Additionally, the words "herein," "above," "below," and words of similar import, when used in this application, refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the technology provided herein can be applied to other systems, not necessarily the system described below. The elements and acts of the various examples described below can be combined to provide further implementations of the technology. Some alternative implementations of the technology may include not only additional elements to those implementations noted below, but also may include fewer elements.

These and other changes can be made to the technology in light of the following detailed description. While the description describes certain examples of the technology, and describes the best mode contemplated, no matter how detailed the description appears, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while some aspect of the technology may be recited as a computer-readable medium claim, other aspects may likewise be embodied as a computer-readable medium claim, or in other forms, such as being embodied in a means-plus-function claim.

In the following description, for the purposes of explanation, numerous specific details are set forth in order to provide a thorough understanding of implementations of the disclosed technology. It will be apparent, however, to one skilled in the art that embodiments of the disclosed technology may be practiced without some of these specific details.

FIG. 1 illustrates an OPD according to some embodiments of the present disclosure. The OPD comprises a cathode 103, an anode 107 and a bulk heterojunction layer 105 disposed between the anode and the cathode. The OPD may be supported on a substrate 101, optionally a glass or plastic substrate.

FIG. 1 illustrates an arrangement in which the cathode is disposed between the substrate and the anode. In other embodiments, the anode may be disposed between the cathode and the substrate.

The bulk heterojunction layer comprises a mixture of an electron acceptor of formula (I) and an electron donor. In some embodiments, the bulk heterojunction layer consists of the electron acceptor of formula (I) and the electron donor. In some embodiments, the bulk heterojunction layer comprises a further electron acceptor other than the electron acceptor of formula (I). Optionally, the further electron acceptor is a fullerene.

Each of the anode and cathode may independently be a single conductive layer or may comprise a plurality of layers.

The OPD may comprise layers other than the anode, cathode and bulk shown in FIG. 1. In some embodiments, a hole-transporting layer is disposed between the anode and the bulk heterojunction layer. In some embodiments, an electron-transporting layer is disposed between the cathode and the bulk heterojunction layer. In some embodiments, a work function modification layer is disposed between the bulk heterojunction layer and the anode, and/or between the bulk heterojunction layer and the cathode.

In use, the photodetectors as described in this disclosure may be connected to a voltage source for applying a reverse bias to the device and/or a device configured to measure photocurrent. The voltage applied to the photodetectors may be variable. In some embodiments, the photodetector may be continuously biased when in use.

In some embodiments, a photodetector system comprises a plurality of photodetectors as described herein, such as an image sensor of a camera.

In some embodiments, a sensor may comprise an OPD as described herein and a light source wherein the OPD is configured to receive light emitted from the light source.

In some embodiments, the light from the light source may or may not be changed before reaching the OPD. For example, the light may be filtered, down-converted or up-converted before it reaches the OPD.

In some embodiments, the light source has a peak wavelength of greater than 750 nm, optionally greater than 950 nm, optionally less than 1500 nm.

The bulk heterojunction layer may contain an electron acceptor (n-type) compound of formula (I):

each $R^{11}$-$R^{14}$ is, independently in each occurrence, H or a substituent with the proviso that at least one occurrence of at least one of $R^{11}$-$R^{14}$ is CN;

each Y is independently O or S;

$Z^1$ is a direct bond or $Z^1$, together with $R^4$ or $R^5$, forms an aromatic or heteroaromatic group $Ar^1$;

Z is a direct bond or, together with R or R, forms an aromatic or heteroaromatic group $Ar^2$;

$Z^3$ is a direct bond or, together with $R^6$, forms an aromatic or heteroaromatic group $Ar^3$; and $Z^4$ is a direct bond or, together with $R^9$, forms an aromatic or heteroaromatic group $Ar^4$.

Optionally, $R^1$ and $R^2$ independently in each occurrence are selected from:

linear, branched or cyclic $C_{1-20}$ alkyl wherein one or more non-adjacent, non-terminal C atoms may be replaced by O, S, $NR^{15}$, CO or COO wherein $R^{15}$ is a $C_{1-12}$ hydrocarbyl and one or more H atoms of the $C_{1-20}$ alkyl may be replaced with F;

a group of formula (Ak)p-(Ar)q wherein Ak is a $C_{1-12}$ alkylene chain in which one or more C atoms may be replaced with O, S, CO or COO; p is 0 or 1; Ar in each occurrence is independently an aromatic or heteroaromatic group which is unsubstituted or substituted with one or more substituents; and q is at least 1, optionally 1, 2 or 3.

By "non-terminal" C atom of an alkyl group as used herein is meant a C atom of the alkyl other than the methyl C atom of a linear (n-alkyl) chain or the methyl C atoms of a branched alkyl chain.

$C_{1-12}$ hydrocarbyl as described anywhere herein may be $C_{1-12}$ alkyl; unsubstituted phenyl; and phenyl substituted with one or more $C_{1-6}$ alkyl groups.

Ar is preferably phenyl.

Where present, substituents of Ar may be a substituent $R^{16}$ wherein $R^{16}$ in each occurrence is independently selected from $C_{1-20}$ alkyl wherein one or more non-adjacent,

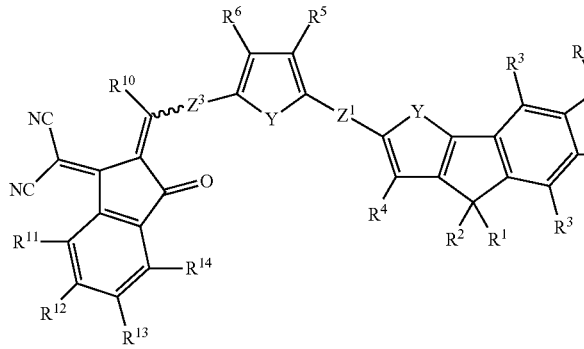 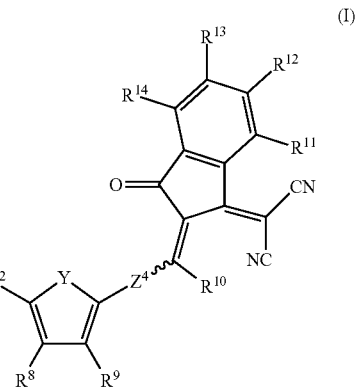

(I)

wherein:
each $R^1$ and $R^2$ is, independently in each occurrence, a substituent;
each $R^3$ is, independently in each occurrence, H or a substituent;
$R^4$-$R^9$ are, independently, H or a substituent;
each $R^{10}$ is, independently in each occurrence, H or a substituent;

non-terminal C atoms may be replaced by O, S, NR, CO or COO and one or more H atoms of the $C_{1-20}$ alkyl may be replaced with F.

If p is 3 or more then -(Ar)p may be a linear or branched chain of Ar groups. A linear chain of Ar groups as described herein has only on monovalent terminal Ar group whereas a branched chain of Ar groups has at least two monovalent terminal Ar groups.

Preferably, $R^1$ and $R^2$ are each selected from $C_{1-20}$ alkyl; unsubstituted phenyl; and phenyl which is unsubstituted or substituted with one or more substituents selected from $R^{16}$.

Optionally, each $R^3$-$R^{10}$ is independently selected from:
H;
$C_{1-12}$ alkyl wherein one or more non-adjacent, non-terminal C atoms may be replaced with O, S, COO or CO; and
an aromatic or heteroaromatic group $Ar^5$, optionally phenyl, which is unsubstituted or substituted with one or more substituents.

The one or more substituents of $Ar^5$, if present, may be selected from $C_{1-12}$ alkyl wherein one or more non-adjacent, non-terminal C atoms may be replaced with O, S, COO or CO.

In some embodiments, each $R^3$-$R^{10}$ is H; $C_{1-20}$ alkyl; or $C_{1-20}$ alkoxy.

In some embodiments at least one occurrence of at least one of $R^3$-$R^{10}$ is not H.

In some embodiments at least one of, optionally both of, $R^5$ and $R^8$ is not H, and each $R^3$, $R^4$ and $R^6$-$R^{10}$ is H.

Optionally, each $R^{12}$ and/or each $R^{13}$ is CN.

Optionally, each $R^{11}$-$R^{14}$ which is not CN is H or a $C_{1-6}$ alkyl group.

Optionally, each $R^{11}$ and each $R^{14}$ is H.

In some embodiments, each $Z^1$-$Z^4$ is a direct bond.

In embodiments where one or more of $Z^1$-$Z^4$ forms part of an aromatic or heteroaromatic group $Ar^1$-$Ar^4$, respectively, each $Ar^1$-$Ar^4$ (where present) is preferably a thiophene.

$Ar^1$-$Ar^4$ are each independently unsubstituted or substituted with one or more substituents. Optionally, substituents of $Ar^1$-$Ar^4$ are selected from $C_{1-12}$ alkyl wherein one or more non-adjacent, non-terminal C atoms may be replaced with O, S, COO or CO.

Optionally, the compound of formula (I) has formula (Ia):

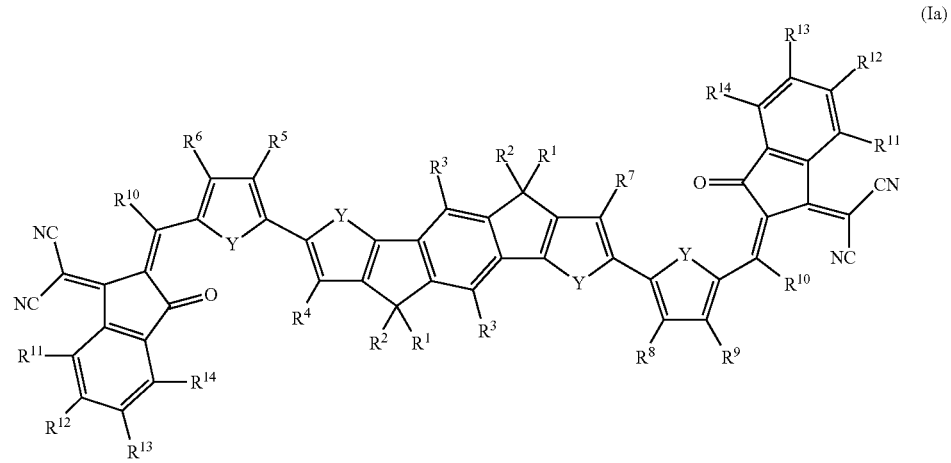

(Ia)

Exemplary compounds of formula (I) are:

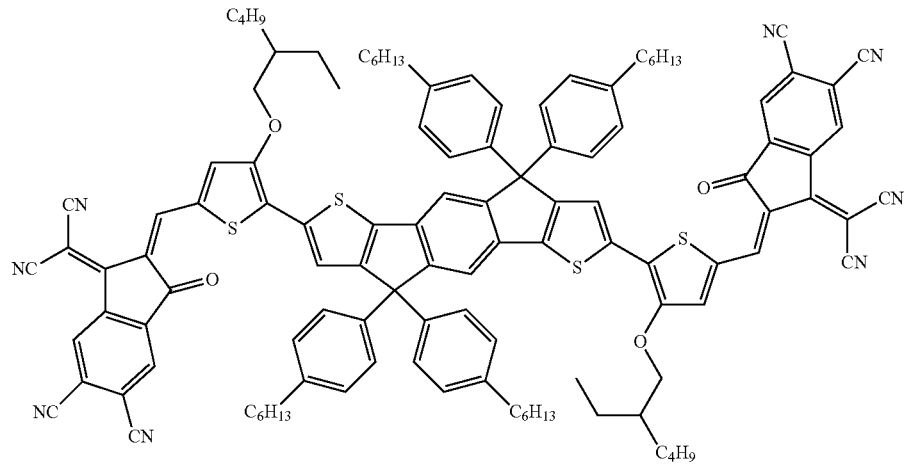

The compound of formula (I) may be used in combination with a fullerene acceptor.

The compound of formula (I): fullerene acceptor weight ratio may be in the range of about 1:0.1-1:1, preferably in the range of about 1:0.1-1:0.5.

The fullerene may be a $C_{60}$, $C_{70}$, $C_{76}$, $C_{78}$ or $C_{84}$ fullerene or a derivative thereof including, without limitation, PCBM-type fullerene derivatives (including phenyl-C61-butyric acid methyl ester ($C_{60}$PCBM) and phenyl-C71-butyric acid methyl ester ($C_{70}$PCBM)), TCBM-type fullerene derivatives (e.g. tolyl-C61-butyric acid methyl ester ($C_{60}$TCBM)), and ThCBM-type fullerene derivatives (e.g. thienyl-C61-butyric acid methyl ester ($C_{60}$ThCBM)

Where present, a fullerene acceptor may have formula (III):

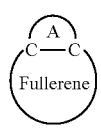

(III)

wherein A, together with the C—C group of the fullerene, forms a monocyclic or fused ring group which may be unsubstituted or substituted with one or more substituents.

Exemplary fullerene derivatives include formulae (IIIa), (IIIb) and (IIIc):

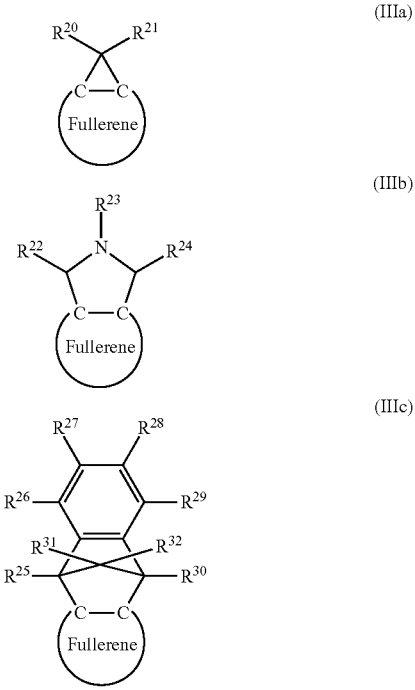

wherein $R^{20}$-$R^{32}$ are each independently H or a substituent.

Substituents $R^{20}$-$R^{32}$ are optionally and independently in each occurrence selected from the group consisting of aryl or heteroaryl, optionally phenyl, which may be unsubstituted or substituted with one or more substituents; and $C_{1-20}$ alkyl wherein one or more non-adjacent, non-terminal C atoms may be replaced with O, S, CO or COO and one or more H atoms may be replaced with F.

Substituents of aryl or heteroaryl groups $R^{20}$-$R^{32}$, where present, are optionally selected from $C_{1-12}$ alkyl wherein one or more non-adjacent, non-terminal C atoms may be replaced with O, S, CO or COO and one or more H atoms may be replaced with F.

The donor (p-type) compound is not particularly limited and may be appropriately selected from electron donating materials that are known to the person skilled in the art, including organic polymers and non-polymeric organic molecules. The p-type compound has a HOMO deeper (further from vacuum) than a LUMO of the compound of formula (I). Optionally, the gap between the HOMO level of the p-type donor and the LUMO level of the n-type acceptor compound of formula (I) is less than 1.4 eV.

In a preferred embodiment the p-type donor compound is an organic conjugated polymer, which can be a homopolymer or copolymer including alternating, random or block copolymers. Preferred are non-crystalline or semi-crystalline conjugated organic polymers. Further preferably the p-type organic semiconductor is a conjugated organic polymer with a low bandgap, typically between 2.5 eV and 1.5 eV, preferably between 2.3 eV and 1.8 eV.

Optionally, the p-type donor has a HOMO level no more than 5.5 eV from vacuum level. Optionally, the p-type donor has a HOMO level at least 4.1 eV from vacuum level.

As exemplary p-type donor polymers, polymers selected from conjugated hydrocarbon or heterocyclic polymers including polyacene, polyaniline, polyazulene, polybenzofuran, polyfluorene, polyfuran, polyindenofluorene, polyindole, polyphenylene, polypyrazoline, polypyrene, polypyridazine, polypyridine, polytriarylamine, poly(phenylene vinylene), poly(3-substituted thiophene), poly(3,4-bisubstituted thiophene), polyselenophene, poly(3-substituted selenophene), poly(3,4-bisubstituted selenophene), poly(bisthiophene), poly(terthiophene), poly(bisselenophene), poly(terselenophene), polythieno[2,3-b]thiophene, polythieno[3,2-b]thiophene, polybenzothiophene, polybenzo[1,2-b:4,5-b']dithiophene, polyisothianaphthene, poly(monosubstituted pyrrole), poly(3,4-bisubstituted pyrrole), poly-1,3,4-oxadiazoles, polyisothianaphthene, derivatives and co-polymers thereof may be mentioned. Preferred examples of p-type donors are copolymers of polyfluorenes and polythiophenes, each of which may be substituted, and polymers comprising benzothiadiazole-based and thiophene-based repeating units, each of which may be substituted. It is understood that the p-type donor may also consist of a mixture of a plurality of electron donating materials.

Optionally, the donor polymer comprises a repeat unit of formula (IV):

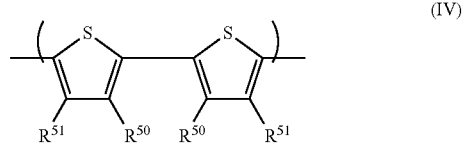

(IV)

wherein $R^{50}$ and $R^{51}$ independently in each occurrence is H or a substituent.

Substituents $R^{50}$ and $R^{51}$ may be selected from groups other than H described with respect to $R^3$-$R^{10}$.

Preferably, each $R^{50}$ is a substituent. In a preferred embodiment, the $R^{50}$ groups are linked to form a group of formula —$Z^1$—$C(R^{52})_2$— wherein $Z^1$ is O, $NR^{53}$, or $C(R^{52})_2$; $R^{52}$ in each occurrence is H or a substituent, preferably a substituent as described with reference to R, most preferably a $C_{1-30}$ hydrocarbyl group; and R is a substituent, preferably a $C_{1-30}$ hydrocarbyl group.

Preferably, each $R^{51}$ is H.

Optionally, the donor polymer comprises a repeat unit of formula (V):

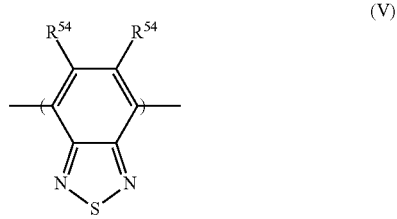

wherein $R^{54}$ in each occurrence is independently H or a substituent. Optionally, substituents $R^{54}$ are selected from the group consisting of F, CN, $NO_2$, and $C_{1-20}$ alkyl wherein one or more non-adjacent, non-terminal C atoms may be replaced with O, S, CO or COO and one or more H atoms may be replaced with F.

Exemplary donor materials are disclosed in, for example, WO2013/051676, the contents of which are incorporated herein by reference.

In some embodiments, the weight of the donor compound to the acceptor compound is from about 1:0.5 to about 1:2.

Preferably, the weight ratio of the donor compound to the acceptor compound is about 1:1 or about 1:1.5.

At least one of the first and second electrodes is transparent so that light incident on the device may reach the bulk heterojunction layer. In some embodiments, both of the first and second electrodes are transparent.

Each transparent electrode preferably has a transmittance of at least 70%, optionally at least 80%, to wavelengths in the range of 300-900 nm.

In some embodiments, one electrode is transparent and the other electrode is reflective.

Optionally, the transparent electrode comprises or consists of a layer of transparent conducting oxide, preferably indium tin oxide or indium zinc oxide. In preferred embodiments, the electrode may comprise poly 3,4-ethylenedioxythiophene (PEDOT). In other preferred embodiments, the electrode may comprise a mixture of PEDOT and polystyrene sulfonate (PSS). The electrode may consist of a layer of PEDOT:PSS.

Optionally, the reflective electrode may comprise a layer of a reflective metal. The layer of reflective material may be aluminium or silver or gold. In some embodiments, a bi-layer electrode may be used. For example, the electrode may be an indium tin oxide (ITO)/silver bi-layer, an ITO/aluminium bi-layer or an ITO/gold bi-layer.

The device may be formed by forming the bulk heterojunction layer over one of the anode and cathode supported by a substrate and depositing the other of the anode or cathode over the bulk heterojunction layer.

The area of the OPD may be less than about 3 $cm^2$, less than about 2 $cm^2$, less than about 1 $cm^2$, less than about 0.75 $cm^2$, less than about 0.5 $cm^2$ or less than about 0.25 $cm^2$. The substrate may be, without limitation, a glass or plastic substrate. The substrate can be described as an inorganic semiconductor. In some embodiments, the substrate may be silicon. For example, the substrate can be a wafer of silicon.

The substrate is transparent if, in use, incident light is to be transmitted through the substrate and the electrode supported by the substrate.

The substrate supporting one of the anode and cathode may or may not be transparent if, in use, incident light is to be transmitted through the other of the anode and cathode.

The bulk heterojunction layer may be formed by any process including, without limitation, thermal evaporation and solution deposition methods.

Preferably, the bulk heterojunction layer is formed by depositing a formulation comprising the acceptor material and the electron donor material dissolved or dispersed in a solvent or a mixture of two or more solvents. The formulation may be deposited by any coating or printing method including, without limitation, spin-coating, dip-coating, roll-coating, spray coating, doctor blade coating, wire bar coating, slit coating, ink jet printing, screen printing, gravure printing and flexographic printing.

The one or more solvents of the formulation may optionally comprise or consist of benzene substituted with one or more substituents selected from chlorine, $C_{1-10}$ alkyl and $C_{1-10}$ alkoxy wherein two or more substituents may be linked to form a ring which may be unsubstituted or substituted with one or more $C_{1-6}$ alkyl groups, optionally toluene, xylenes, trimethylbenzenes, tetramethylbenzenes, anisole, indane and its alkyl-substituted derivatives, and tetralin and its alkyl-substituted derivatives.

The formulation may comprise a mixture of two or more solvents, preferably a mixture comprising at least one benzene substituted with one or more substituents as described above and one or more further solvents. The one or more further solvents may be selected from esters, optionally alkyl or aryl esters of alkyl or aryl carboxylic acids, optionally a $C_{1-10}$ alkyl benzoate, benzyl benzoate or dimethoxybenzene. In preferred embodiments, a mixture of trimethylbenzene and benzyl benzoate is used as the solvent. In other preferred embodiments, a mixture of trimethylbenzene and dimethoxybenzene is used as the solvent.

The formulation may comprise further components in addition to the electron acceptor, the electron donor and the one or more solvents. As examples of such components, adhesive agents, defoaming agents, deaerators, viscosity enhancers, diluents, auxiliaries, flow improvers colourants, dyes or pigments, sensitizers, stabilizers, nanoparticles, surface-active compounds, lubricating agents, wetting agents, dispersing agents and inhibitors may be mentioned.

The organic photodetector as described herein may be used in a wide range of applications including, without limitation, detecting the presence and/or brightness of ambient light and in a sensor comprising the organic photodetector and a light source. The photodetector may be configured such that light emitted from the light source is incident on the photodetector and changes in wavelength and/or brightness of the light may be detected, e.g. due to absorption by and/or emission of light from a target material in a sample disposed in a light path between the light source and the organic photodetector. The sensor may be, without limitation, a gas sensor, a biosensor, an X-ray imaging device, an image sensor such as a camera image sensor, a motion sensor (for example for use in security applications) a proximity sensor or a fingerprint sensor. A 1D or 2D photosensor array may comprise a plurality of photodetectors as described herein in an image sensor. The photodetector may be configured to detect light emitted from a target analyte which emits light upon irradiation by the light source or which is bound to a luminescent tag which emits light upon irradiation by the light source. The photodetector may be configured to detect a wavelength of light emitted by the target analyte or a luminescent tag bound thereto.

EXAMPLES

Synthesis

Compound Example 1 was prepared according to the following reaction scheme:

and cone HCl (75 mL) was added followed by 5N HCl (200 mL). The mixture was heated to 75° C. for 1 h. After cooling the organics were extracted in DCM (3×100 mL). The combined organics were dried, filtered and concentrated to yield 43 g of crude material. The crude was triturated with acetone (300 mL) for 1 h and the obtained solid was isolated by filtration to give 22 g of stage 2 material.

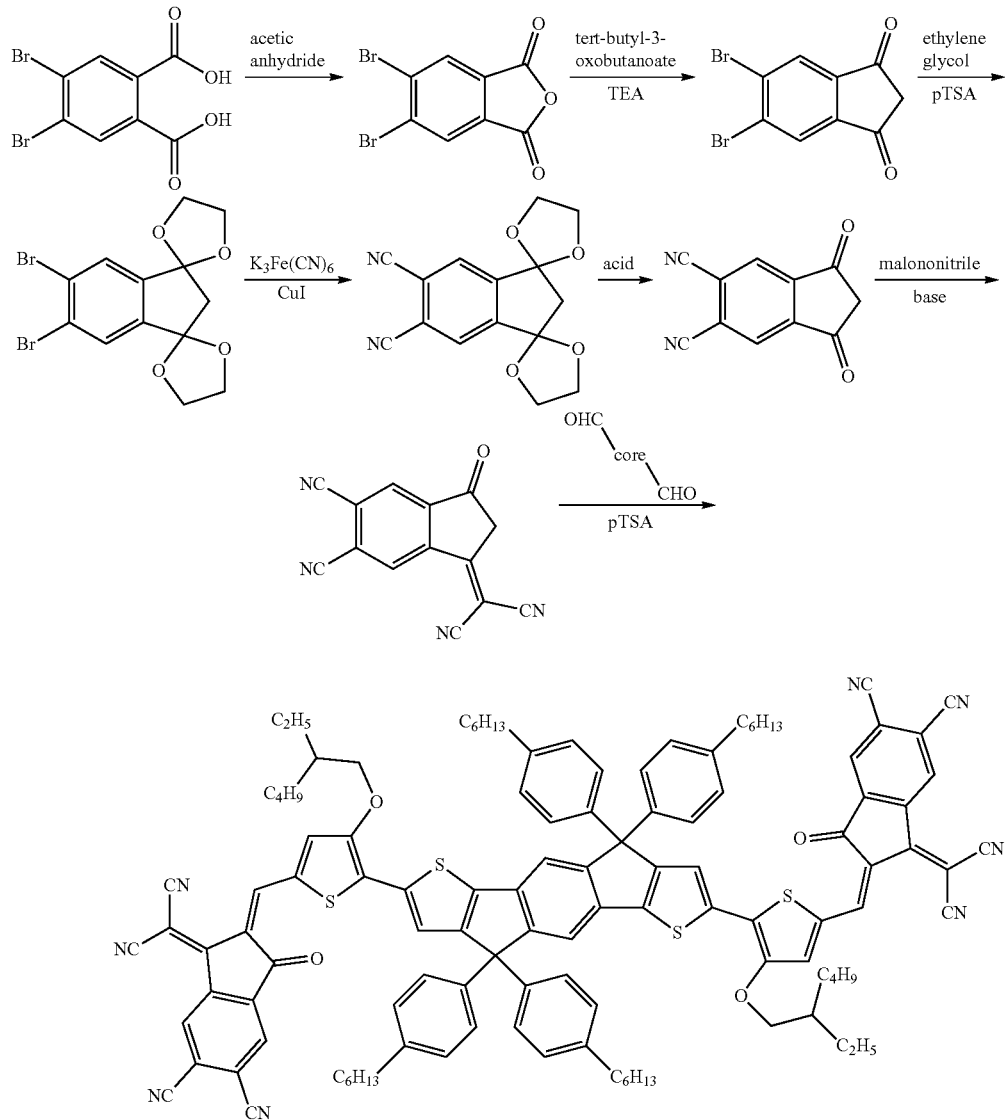

Compound Example 1

Step 1

4,5-Dibromophthalic acid (48 g) was dissolved in acetic anhydride (240 mL) and heated to 130° C. for 4 h. After cooling the obtained solid was isolated by filtration and washed with toluene (20 mL). The material (40 g) was used in the next step without further purification.

Step 2

Stage 1 crude material (40 g) was dissolved in acetic anhydride (100 mL) and trimethylamine (60 mL). tert-Butylacetoacetate (20.5 g, 130 mmol) was added and the reaction was stirred at room temperature for 16 h. Ice (75 g)

Step 3

Stage 2 material (22 g), ethane-1,2-diol (44.8 g, 723 mmol) and p-toluenesulfonic acid (1.24 g, 7.23 mL) was dissolved in toluene (600 mL) and heated to 125° C. for 20 h. After cooling the volatiles were removed and the crude product was purified by column chromatography on silica eluting with 20% ethyl acetate in hexanes. The product was again treated with ethane-1,2-diol (44.8 g, 723 mmol) and PTSA (1.24 g, 7.23 mmol) in toluene (600 mL) at 125° C. for 20 h. After cooling the volatiles were removed and the crude material was triturated with hexanes (200 mL) for 2 h to isolate the product as a pale orange solid (23 g) which was used without further purification.

Step 4

Stage 3 crude material (23 g, potassium hexacyanoferrate (15.4 g, 4638 mmol), 1-butylimidazole (15.2 g, 123 mmol) and copper(I) iodide (4.45 g, 23.4 mmol) were suspended in o-xylene (1.2 L) and heated to 140° C. for 40 h. A further portion of copper(I) iodide (4.45 g, 23.4 mmol) was added and heating continued for a further 48 h. The reaction was cooled to 60° C. and filtered through a bed of Celite, washing with ethyl acetate (2×250 mL) and DCM (2×25 mL). The volatiles were removed from the filtrate and the crude residue was purified by column chromatography eluting with 0-45% ethyl acetate in hexanes and then again eluting with 0-35% ethyl acetate in hexanes. The product containing fractions were concentrated to yield the product (6.3 g) which was used in the next step without further purification.

Step 5

1,4-Dioxane (500 mL) was cooled in an ice/methanol bath and purged with HCl gas for 2 h. Stage 4 crude material was added and the reaction mixture was allowed to warm to room temperature. Another 250 mL of HCl-purged 1,4-dioxane (250 mL) was added and the reaction stirred for 48 h. The reaction mixture was purged with nitrogen and the solvent removed. The crude residue was taken to the next step without further purification.

Stage 6

Sodium acetate (10.4 g, 128 mmol) was dissolved in ethanol (150 mL). Malononitrile (12.6 g, 192 mmol) was added and the mixture stirred at room temperature for 30 mins. The mixture was then added to a solution of crude stage 5 material (6.3 g) in ethanol (30 mL) and stirred at room temperature for 16 h. Water (180 mL) was added and the solution was cooled in an ice bath before being acidified to pH 1-2/The organics were extracted with DCM (3×500 mL) and the solvent was removed to yield 13.7 g crude material. This was purified by reverse-phase column chromatography eluting with 0-20% acetonitrile in water. After isolation the product was dissolved in acetonitrile (100 mL), water (200 mL) and 1.5N HCl (25 mL) and stirred for 30 mins before freeze drying. 460 mg was isolated with ~94% purity.

Stage 7

The core (250 mg, 0.18 mmol), stage 6 material (300 mg, 1.80 mmol) and p-toluenesulfonic acid hydrate (309 mg, 1.80 mmol) were heated in ethanol (50 mL) at 65° C. for 16 h. The cooled reaction mixture was filtered and the solid was washed with ethanol before being purified by column chromatography on silica eluting with 50-100% DCM in hexanes. The product-containing fractions were concentrated to yield the product as a dark solid (140 mg) with 98.55% purity.

Compound Example 2

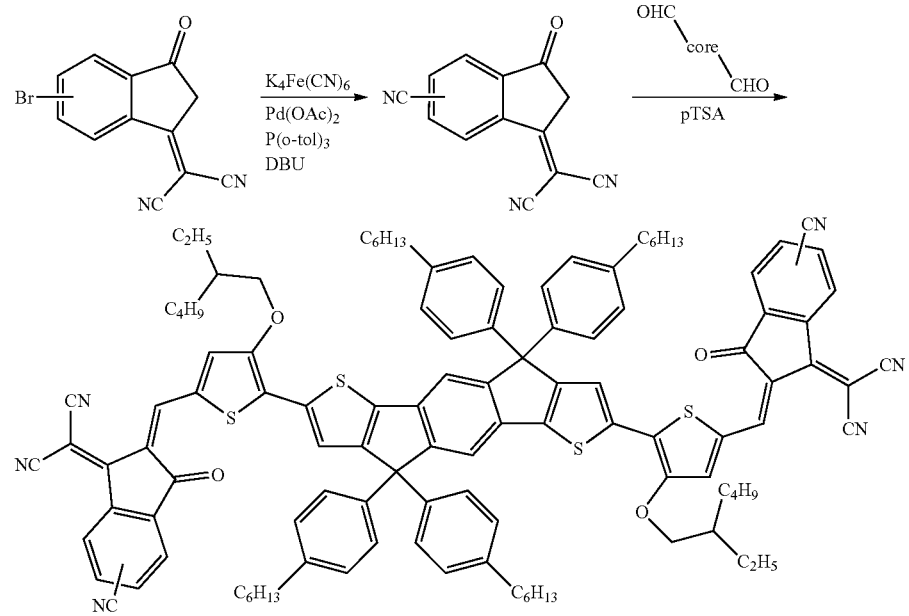

Compound Example 2

The starting material was made via an analogous procedure to Compound Example 1 starting from 4-bromophthalic acid.

Stage 1

Bromide material (4.68 g, 17.1 mmol) was dissolved in dimethyl acetamide and degassed with nitrogen. Potassium ferricyanide (5.74 g, 13.6 mmol), DBU (2.6 g, 17.1 mmol), palladium acetate (767 mg, 3.4 mmol) and tri(o-tolylphosphine) (2.08 g, 6.8 mmol) were added and the mixture stirred at 110° C. for 16 h. After cooling the reaction was quenched with water and extracted with ethyl acetate. The combined organics were washed with water and brine before being dried with sodium sulfate, filtered and concentrated to give a crude material. The crude was columned on silica with DCM-methanol as the eluent. The product-containing fractions were precipitated from DCM-hexane to get the stage 1 material (2 g) with >98% purity.

Stage 2

The core (840 mg, 0.61 mmol), stage 1 material (929 mg, 4.2 mmol) and p-toluenesulfonic acid hydrate (920 mg, 4.8 mmol) were heated in ethanol (50 mL) at 65° C. for 16 h. The cooled reaction mixture was filtered and the solid was washed with ethanol before being purified by column chromatography on silica eluting with 50-100% DCM in petrol ether. The product-containing fractions were concentrated and recrystallized from chloroform-acetonitrile to yield the product as a dark solid (630 mg) with >99% purity as a mixture of isomers.

Modelling Data

LUMO levels and HOMO-LUMO bandgaps of compounds of formula (Ia) were modelled in which $R^1$, $R^2$, $R^6$ and $R^8$ are each methyl; $R^3$, $R^4$, $R^5$, $R^7$, $R^9$ and $R^{10}$ are H and $R^{11}$-$R^{14}$ are as in Table 1.

For comparison, compounds in which CN groups of formula (Ia) are replaced with F were also modelled.

Quantum chemical modelling was performed using Gaussian09 software available from Gaussian using Gaussian09 with B3LYP (functional) and LACVP* (Basis set).

TABLE 1

| Compound | $R^{11}$ | $R^{12}$ | $R^{13}$ | $R^{14}$ | LUMO (eV) | Band gap (eV) |
|---|---|---|---|---|---|---|
| Model Comparative Compound 1 | H | F | H | H | 3.36 | 1.73 |
| Model Compound Example 1 | H | CN | H | H | 3.57 | 1.71 |
| Model Comparative Compound 2 | H | F | F | H | 3.39 | 1.74 |
| Model Compound Example 2 | H | CN | CN | H | 3.81 | 1.62 |

With reference to Table 1, Model Compound Examples 1 and 2 have a LUMO which is deeper (i.e. further from vacuum level) and a smaller band gap than Model Comparative Compounds 1 or 2.

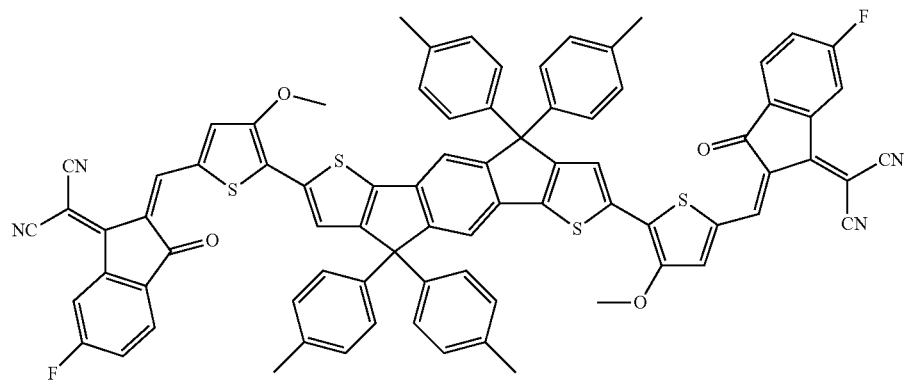 [SMILES: COc1cc(/C=C2\C(=O)c3ccc(F)cc3C2=C(C#N)C#N)sc1-c1cc2c(s1)-c1cc3c(cc1C2(c1ccc(C)cc1)c1ccc(C)cc1)-c1sc(-c2sc(/C=C4\C(=O)c5ccc(F)cc5C4=C(C#N)C#N)cc2OC)cc1C3(c1ccc(C)cc1)c1ccc(C)cc1]

Model Comparative Compound 1

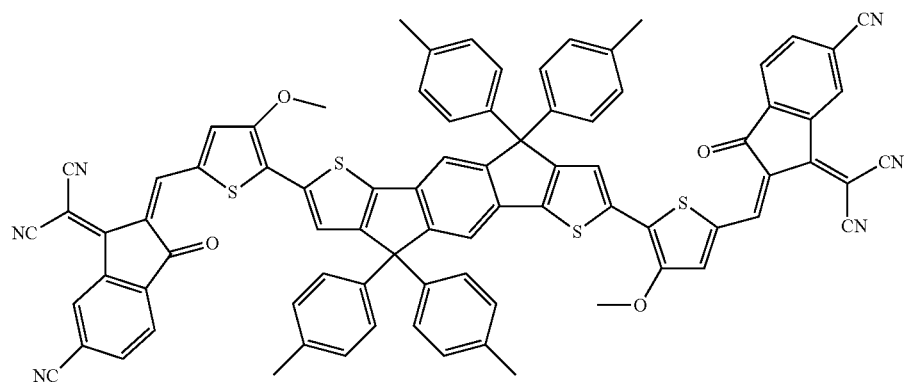 [SMILES: COc1cc(/C=C2\C(=O)c3ccc(C#N)cc3C2=C(C#N)C#N)sc1-c1cc2c(s1)-c1cc3c(cc1C2(c1ccc(C)cc1)c1ccc(C)cc1)-c1sc(-c2sc(/C=C4\C(=O)c5ccc(C#N)cc5C4=C(C#N)C#N)cc2OC)cc1C3(c1ccc(C)cc1)c1ccc(C)cc1]

Figure 2:
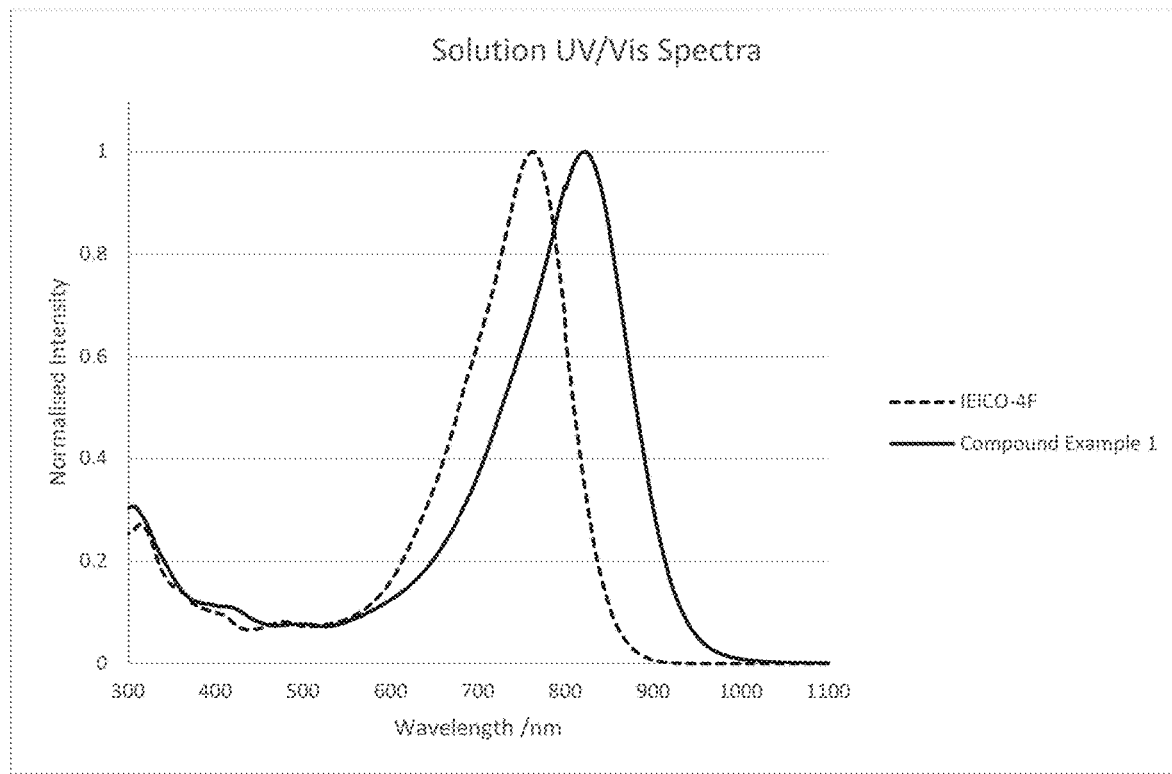
FIG. 2 illustrates absorption spectra for a compound according to some embodiments of the present disclosure and a comparative compound.

Model Compound Example 1
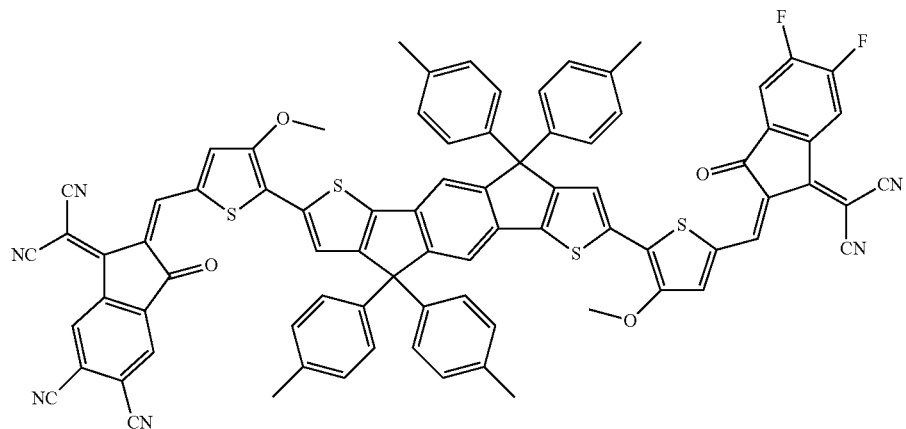 [SMILES: COc1cc(/C=C2\C(=O)c3cc(F)c(F)cc3C2=C(C#N)C#N)sc1-c1cc2c(s1)-c1cc3c(cc1C2(c1ccc(C)cc1)c1ccc(C)cc1)-c1sc(-c2sc(/C=C4\C(=O)c5cc(C#N)c(C#N)cc5C4=C(C#N)C#N)cc2OC)cc1C3(c1ccc(C)cc1)c1ccc(C)cc1]
Model Comparative Compound 2
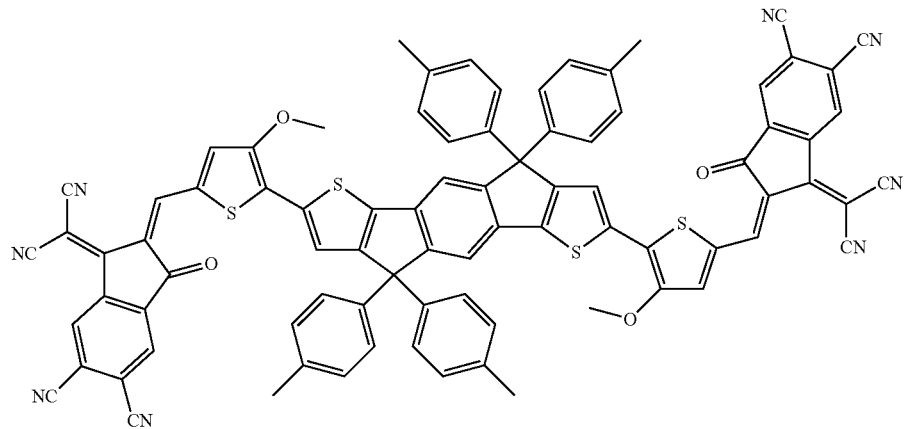 [SMILES: COc1cc(/C=C2\C(=O)c3cc(C#N)c(C#N)cc3C2=C(C#N)C#N)sc1-c1cc2c(s1)-c1cc3c(cc1C2(c1ccc(C)cc1)c1ccc(C)cc1)-c1sc(-c2sc(/C=C4\C(=O)c5cc(C#N)c(C#N)cc5C4=C(C#N)C#N)cc2OC)cc1C3(c1ccc(C)cc1)c1ccc(C)cc1]
Model Compound Example 2
Absorption
FIG. 2 shows absorption spectra for Compound Example 1 and comparative compound IEICO-4F, in which the CN groups $R^{12}$ and $R^{13}$ of Compound Example 1 are replaced with F:
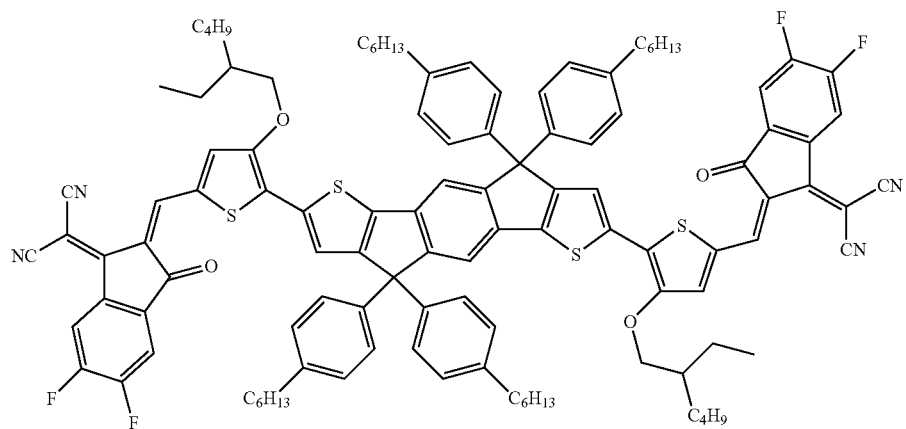

IEICO-4F Compound Example 1 has a significantly longer peak wavelength (822 nm) than comparative compound IEICO-4F (762 nm).

HOMO and LUMP Energy Levels

HOMO and LUMO levels of films of Compound Example 1 and comparative compound IEICO-4F were determined by square wave voltammetry (SWV) and the results are set out in Table 2.

In line with the above modelling data, the LUMO level of Compound 1 is deeper and its HOMO-LUMO gap is smaller as compared to comparative compound IEICO-4F.

TABLE 2

|  | Film HOMO/eV | Film LUMO/eV | HOMO-LUMO gap (eV) |
| --- | --- | --- | --- |
| Compound Example 1 | −5.44 | −4.30 | 1.14 |
| Compound Example 2 | −5.46 | −4.11 | 1.35 |
| IEICO-4F (comparative) | −5.45 | −4.03 | 1.42 |

The LUMO energy levels of compounds reported herein were determined from films of the compounds using SWV at room temperature. In SWV, the current at a working electrode is measured while the potential between the working electrode and a reference electrode is swept linearly in time. The difference current between a forward and reverse pulse is plotted as a function of potential to yield a voltammogram. The apparatus to measure HOMO or LUMO energy levels by SWV may comprise a cell containing tertiary butyl ammonium perchlorate or tertiary butyl ammonium hexafluorophosphate in acetonitrile; a glassy carbon working electrode; a platinum counter electrode and a leak free Ag/AgCl reference electrode.

Ferrocene is added directly to the existing cell at the end of the experiment for calculation purposes where the potentials are determined for the oxidation and reduction of ferrocene versus Ag/AgCl using cyclic voltammetry (CV).

Apparatus:

CHI 660D Potentiostat.

3 mm Diameter glassy carbon working electrode Leak free Ag/AgCl reference electrode Pt wire auxiliary or counter electrode.

0.1 M Tetrabutylammonium hexafluorophosphate in acetonitrile.

Method:

The sample is dissolved in Toluene (3 mg/ml) and spun at 3000 rpm directly on to the glassy carbon working electrode.

$$LUMO = 4.8 - E \text{ ferrocene (peak to peak average)} - E \text{ reduction of sample (peak maximum)}.$$

$$HOMO = 4.8 - E \text{ ferrocene (peak to peak average)} + E \text{ oxidation of sample (peak maximum)}.$$

A typical SWV experiment runs at 15 Hz frequency; 25 mV amplitude and 0.004 V increment steps. Results are calculated from 3 freshly spun film samples for both the HOMO and LUMO data.

All experiments are run under an Argon gas purge.

Device Example 1

A device having the following structure was prepared:
Cathode/Donor: Acceptor layer/Anode A glass substrate coated with a layer of indium-tin oxide (ITO) was treated with polyethyleneimine (PEIE) to modify the work function of the ITO.

A ca. 300 nm thick bulk heterojunction layer of a mixture of Donor Polymer 1 and Compound Example 1 was deposited over the modified ITO layer by bar coating from a 1,2,4 Trimethylbenzene; Dimethoxybenzene 95:5 v/v solvent mixture in a donor/acceptor mass ratio of 1:1.5.

An anode (Clevios HIL-E100) available from Heraeus was formed over the donor/acceptor mixture layer by spin-coating.

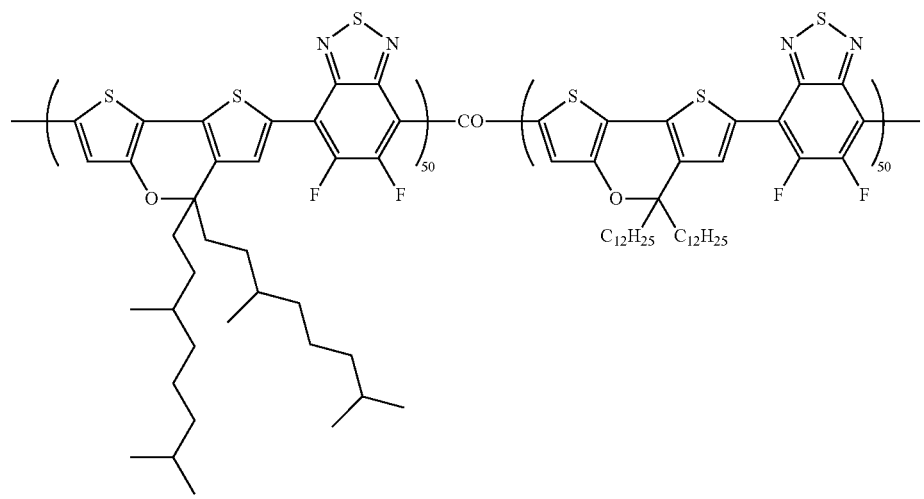

Donor Polymer 1
Comparative Device 1A

A device was prepared as described for Device Example 1 except that Compound Example 1 was replaced with IEICO-4F in a bulk heterojunction layer having a thickness of about 500 nm.

Comparative Device 1B

A device was prepared as described for Device Example 1 except that Compound Example 1 was replaced with fullerene acceptor C70-IPH in a bulk heterojunction layer having a thickness of about 500 nm.

Figure 3:
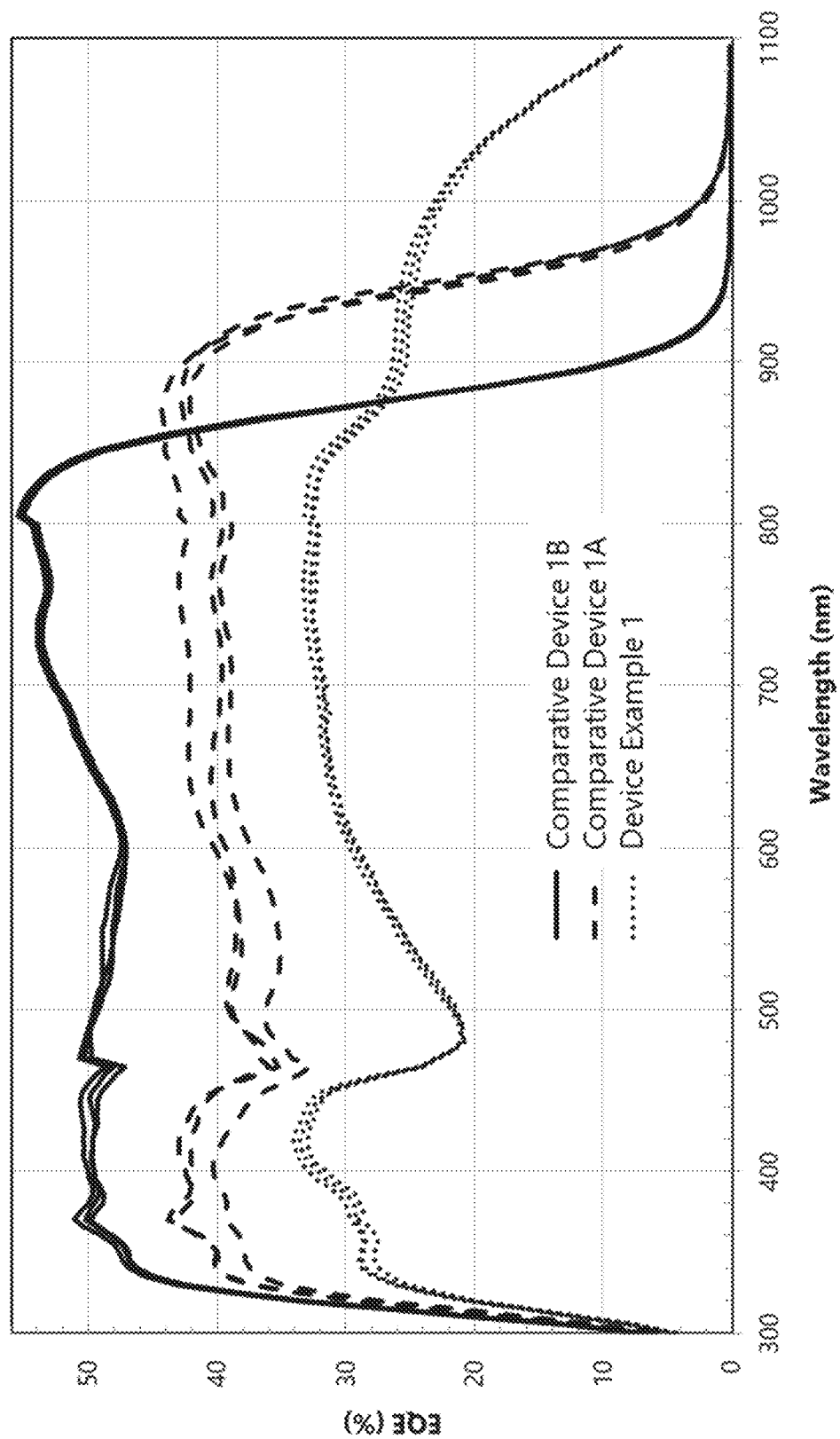
FIG. 3 shows external quantum efficiencies of an OPD according to some embodiments of the present disclosure containing Compound Example 1 compared to a comparative OPD containing acceptor IEICO-4F and a comparative OPD containing a fullerene acceptor.

With reference to FIG. 3, Device Example 1 has significantly higher external quantum efficiency compared to Comparative Device 1A at wavelengths above about 950 nm and Comparative Device 1B at wavelengths above about 900 nm.

Device Example 2A

A device was prepared as described for Device Example 1 with a ca. 500 nm thick bulk heterojunction layer.

Device Example 2B

A device was prepared as described for Device Example 2A except that Compound Example 2 was used in place of Compound Example 1.

Figure 4:
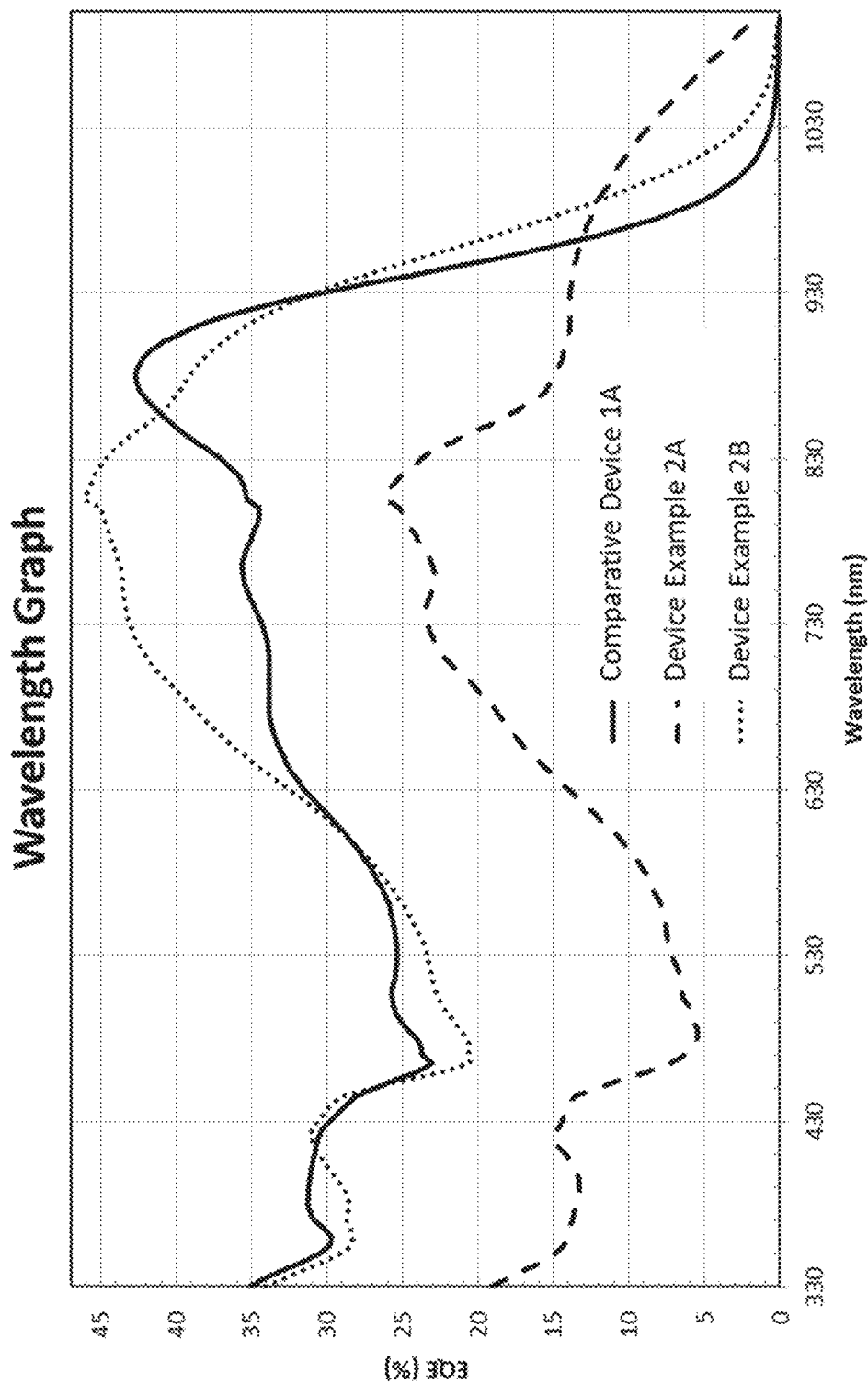
FIG. 4 shows external quantum efficiencies of an OPD according to some embodiments of the present disclosure containing Compound Example 1; an OPD according to some embodiments of the present disclosure containing Compound Example 2; and a comparative OPD containing acceptor IEICO-4F.

With reference to FIG. 4, Device Examples 2A and 2B have significantly higher external quantum efficiency than Comparative Device 1A at wavelengths above about 950 nm.

Device Example 3

A device was prepared as described for Device Example 2A except that the bulk heterojunction layer further contains fullerene acceptor $C_{70}$ PCBM in a ratio of Donor Polymer 1:Compound Example 1:$C_{70}$PCBM in a ratio of 1:1.05:0.45 by weight.

Figure 5:
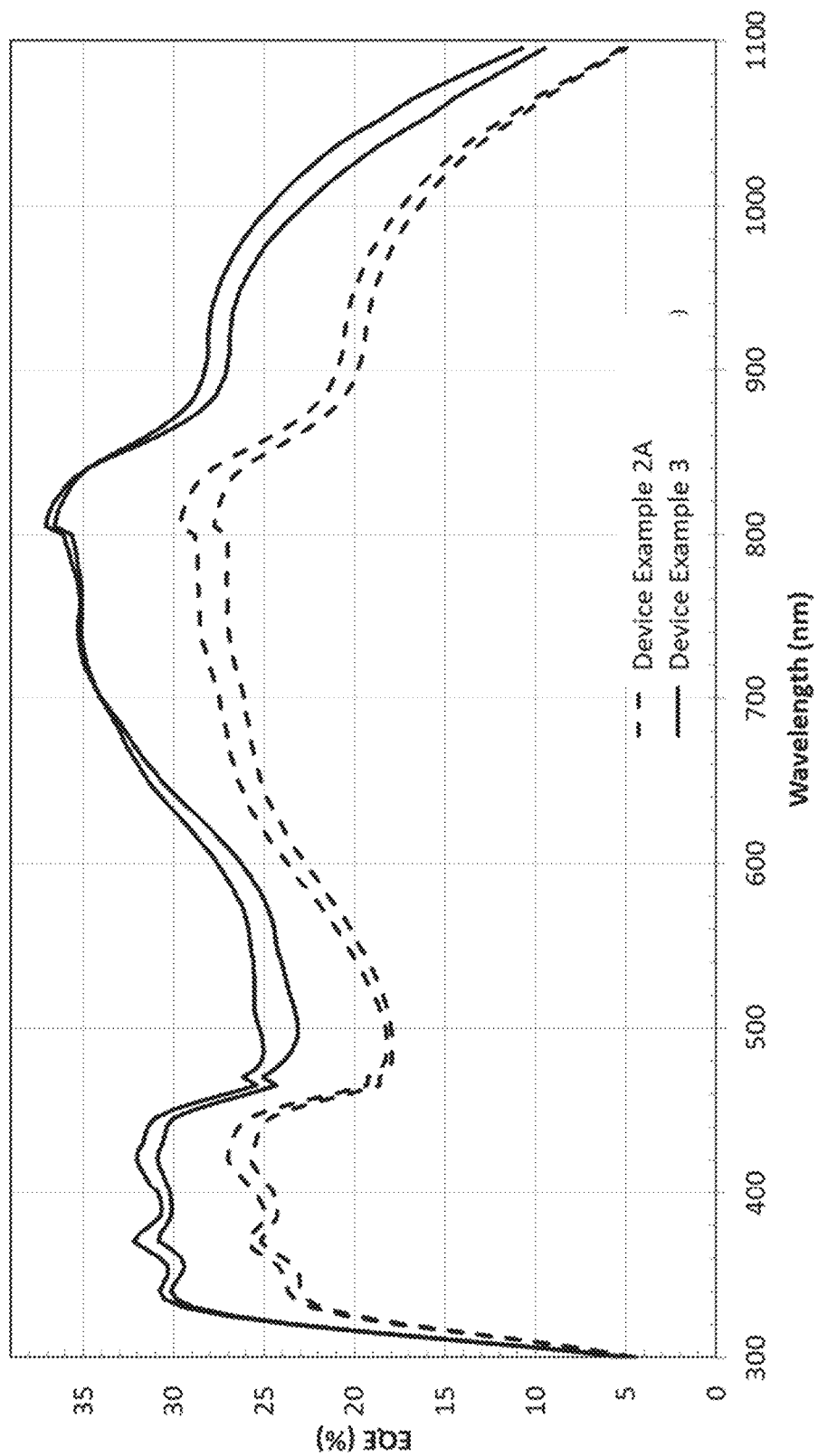
FIG. 5 shows external quantum efficiencies of OPDs according to some embodiments of the present disclosure containing Compound Example 1 with and without a further fullerene acceptor.

With reference to FIG. 5, external quantum efficiency increases upon addition of the further acceptor.

Device Example 4

A device was prepared as described for Device Example 2B except that the bulk heterojunction layer further contains fullerene acceptor $C_{70}$ PCBM in a ratio of Donor Polymer 1:Compound Example 2:$C_{70}$PCBM in a ratio of 1:1.25:0.25 by weight.

Figure 6:
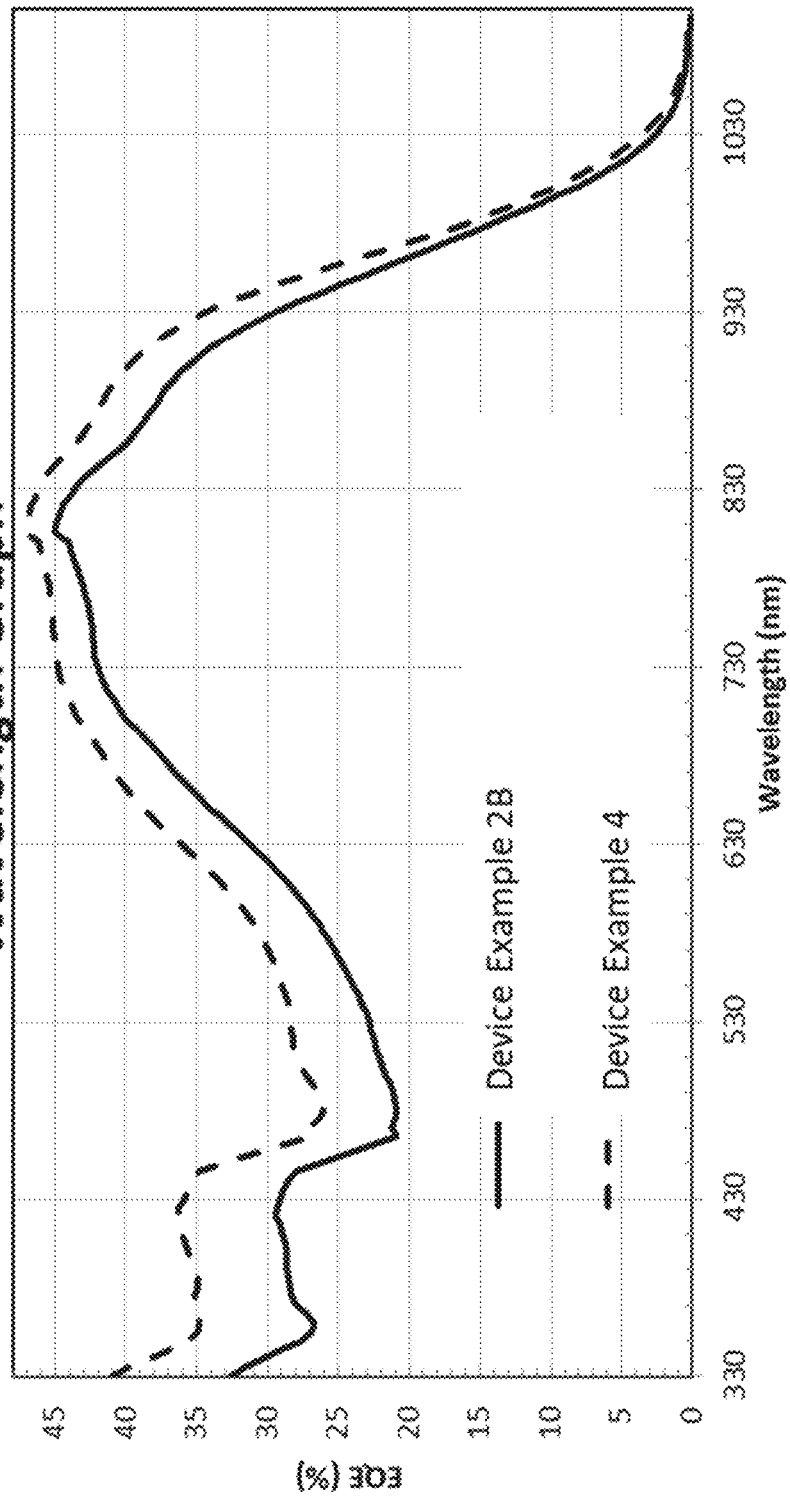
FIG. 6 shows external quantum efficiencies of OPDs according to some embodiments of the present disclosure containing Compound Example 2 with and without a further fullerene acceptor.

With reference to FIG. 6, external quantum efficiency increases upon addition of the further acceptor.

The invention claimed is:

1. A compound of formula (I):

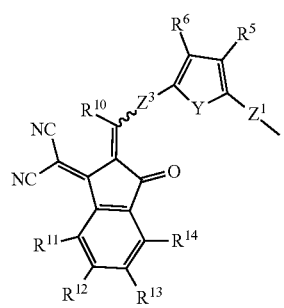

(I)

-continued

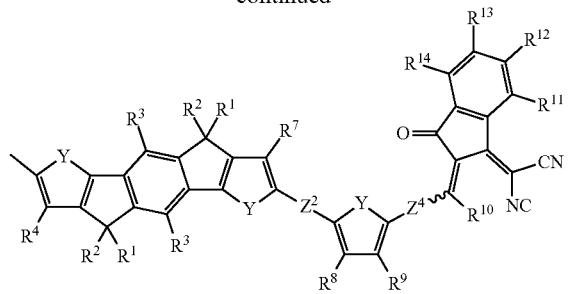

wherein:

each $R^1$ and $R^2$ is, independently in each occurrence, a substituent;

each $R^3$ is, independently in each occurrence, H or a substituent;

$R^4$-$R^9$ are, independently, H or a substituent;

each $R^{10}$ is, independently in each occurrence, H or a substituent;

each $R^{11}$-$R^{14}$ is, independently in each occurrence, H or a substituent with the proviso that at least one occurrence of at least one of $R^{11}$-$R^{14}$ is CN;

each Y is independently O or S;

$Z^1$ is a direct bond or $Z^1$, together with $R^4$ or $R^5$, forms an aromatic or heteroaromatic group $Ar^1$;

$Z^2$ is a direct bond or, together with $R^7$ or $R^8$, forms an aromatic or heteroaromatic group $Ar^2$;

$Z^3$ is a direct bond or, together with $R^6$, forms an aromatic or heteroaromatic group $Ar^3$; and $Z^4$ is a direct bond or, together with $R^9$, forms an aromatic or heteroaromatic group $Ar^4$.

2. A compound according to claim 1 wherein at least one $R^{12}$ group is CN.

3. A compound according to claim 1 wherein at least one $R^{13}$ group is CN.

4. A compound according to claim 1 wherein each $R^{11}$ is H.

5. A compound according to claim 1 wherein each $R^{14}$ is H.

6. A compound according to claim 1 wherein at least one of $Z^1$-$Z^4$ is a direct bond.

7. A compound according to claim 6 wherein each of $Z^1$-$Z^4$ is a direct bond.

8. A compound according to claim 1 wherein the compound of formula (I) has formula (Ia):

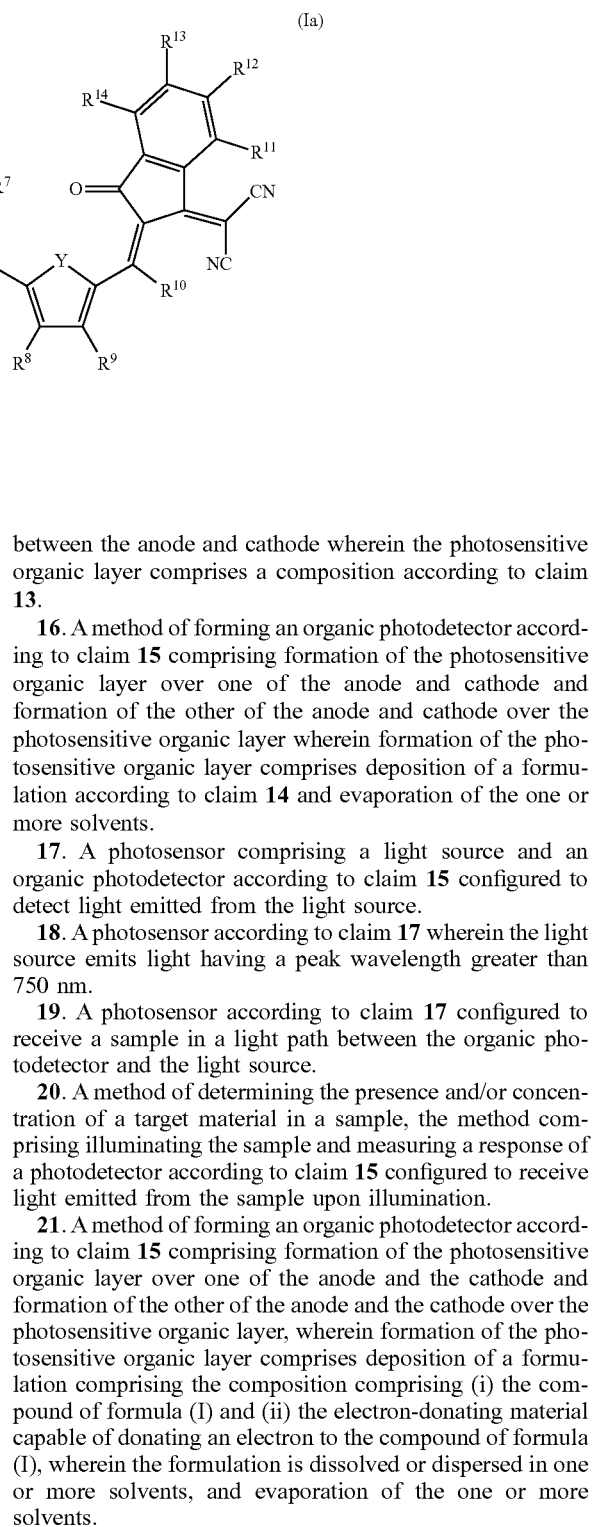

(Ia)

9. A compound according to claim 1 wherein $R^1$ and $R^2$ independently in each occurrence are selected from the group consisting of:
   linear, branched or cyclic $C_{1-20}$ alkyl wherein one or more non-adjacent, non-terminal C atoms may be replaced by O, S, $NR^{15}$, CO or COO wherein $R^{15}$ is a $C_{1-12}$ hydrocarbyl and one or more H atoms of the $C_{1-20}$ alkyl may be replaced with F; and
   a group of formula (Ak)p-(Ar)q wherein Ak is a $C_{1-12}$ alkylene chain in which one or more C atoms may be replaced with O, S, CO or COO; p is 0 or 1; Ar in each occurrence is independently an aromatic or heteroaromatic group which is unsubstituted or substituted with one or more substituents; and q is at least 1.

10. The compound according to claim 9 wherein at least one of $R^1$ and $R^2$ is phenyl which is unsubstituted or substituted with one or more substituents selected from $C_{1-20}$ alkyl wherein one or more non-adjacent, non-terminal C atoms may be replaced by O, S, CO or COO and one or more H atoms of the $C_{1-20}$ alkyl may be replaced with F.

11. The compound according to claim 1 wherein each $R^3$-$R^{10}$ is independently selected from:
    H;
    $C_{1-12}$ alkyl wherein one or more non-adjacent, non-terminal C atoms may be replaced with O, S, COO or CO; and
    an aromatic or heteroaromatic group $Ar^5$ which is unsubstituted or substituted with one or more substituents.

12. The compound according to claim 1 wherein at least one occurrence of at least one of $R^3$-$R^{10}$ is not H.

13. A composition comprising a compound of formula (I) according to claim 1 and an electron-donating material capable of donating an electron to the compound of formula (I).

14. A formulation comprising a compound according to claim 1 or composition according to claim 13 dissolved or dispersed in one or more solvents.

15. An organic photodetector comprising: an anode; a cathode; and a photosensitive organic layer disposed between the anode and cathode wherein the photosensitive organic layer comprises a composition according to claim 13.

16. A method of forming an organic photodetector according to claim 15 comprising formation of the photosensitive organic layer over one of the anode and cathode and formation of the other of the anode and cathode over the photosensitive organic layer wherein formation of the photosensitive organic layer comprises deposition of a formulation according to claim 14 and evaporation of the one or more solvents.

17. A photosensor comprising a light source and an organic photodetector according to claim 15 configured to detect light emitted from the light source.

18. A photosensor according to claim 17 wherein the light source emits light having a peak wavelength greater than 750 nm.

19. A photosensor according to claim 17 configured to receive a sample in a light path between the organic photodetector and the light source.

20. A method of determining the presence and/or concentration of a target material in a sample, the method comprising illuminating the sample and measuring a response of a photodetector according to claim 15 configured to receive light emitted from the sample upon illumination.

21. A method of forming an organic photodetector according to claim 15 comprising formation of the photosensitive organic layer over one of the anode and the cathode and formation of the other of the anode and the cathode over the photosensitive organic layer, wherein formation of the photosensitive organic layer comprises deposition of a formulation comprising the composition comprising (i) the compound of formula (I) and (ii) the electron-donating material capable of donating an electron to the compound of formula (I), wherein the formulation is dissolved or dispersed in one or more solvents, and evaporation of the one or more solvents.

* * * * *